United States Patent [19]

Higashiura et al.

[11] Patent Number: 5,430,052
[45] Date of Patent: Jul. 4, 1995

[54] AMINOALKANESULFONIC ACID DERIVATIVES AND PHARMACEUTICAL COMPOSITIONS FOR USE IN PREVENTING OR TREATING HEART DISEASES

[75] Inventors: Kunihiko Higashiura, Hyogo; Masao Hattori, Kosugi; Kazuharu Ienaga, Hyogo, all of Japan

[73] Assignee: Nippon Zoki Pharmaceutical Co., Ltd., Osaka, Japan

[21] Appl. No.: 167,459

[22] Filed: Dec. 15, 1993

Related U.S. Application Data

[63] Continuation of Ser. No. 731,783, Jul. 18, 1991, abandoned.

[30] Foreign Application Priority Data

Jul. 19, 1990 [JP] Japan .................................. 2-192575
Aug. 23, 1990 [JP] Japan .................................. 2-223807

[51] Int. Cl.$^6$ .................... C07C 309/15; A61K 31/185
[52] U.S. Cl. ..................................... 514/424; 514/428; 548/556; 548/570; 562/104; 562/105; 562/106; 562/107
[58] Field of Search ............. 548/556, 570; 562/104, 562/105, 106, 107; 514/424, 428, 578, 553

[56] References Cited

U.S. PATENT DOCUMENTS 5,011,983 4/1991 Behr ...................................... 562/41

OTHER PUBLICATIONS

Piper, J. Med Chem. 22, 631 (1979).
Ienaga, et al., Chem. Pharm. Bull., 36 (1) 70–77 (1988).
Ienaga, et al., Chem. Pharm. Bull., 36(8) 2796–2801 (1988).
Higashiura, et al., J. Chem Soc. Perkin Trans. 1 (1989) pp. 1479–1481.
Chem. Abs. 101 (7): 54561f (1984).
Takeuchi Comp Biochem Physiol. C 56 63 (1977).
Schwenkkraus Arch Pharm (Weinheim) 323 93 (1990).

*Primary Examiner*—Robert Gerstl
*Attorney, Agent, or Firm*—Armstrong, Westerman, Hattori, McLeland & Naughton

[57] ABSTRACT

The present invention relates to a pharmaceutical composition for use in preventing or treating heart diseases in a mammal, which comprises at least one aminoalkanesulfonic acid derivative of the formula (I):

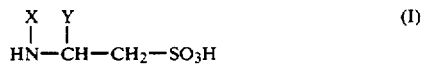

wherein X is hydrogen or an amino acid residue; Y is hydrogen, a phenyl group or an alkyl group, which may have a hydroxy, amino, carboxy, phenyl or hydroxyphenyl group; or X and Y are joined to form a trimethylene or hydroxytrimethylene group; and at least one of X and Y is other than hydrogen;

or pharmaceutically acceptable salt thereof.

5 Claims, 1 Drawing Sheet

AMINOALKANESULFONIC ACID DERIVATIVES AND PHARMACEUTICAL COMPOSITIONS FOR USE IN PREVENTING OR TREATING HEART DISEASES

This application is a continuation of application Ser. No. 07/731,783 filed Jul. 18, 1991, now abandoned.

BACKGROUND OF THE INVENTION

The present invention relates to an aminoalkanesulfonic acid derivative and a pharmaceutical composition for use in preventing or treating heart diseases.

Myocardial cells maintain the homeostasis of calcium through the cell membrane. When the functional disorders of the cell membrane are induced or excessive calcium ions ($Ca^{2+}$) are overloaded in myocardial cells by the drug effects etc., the myocardial cells are obstructed and that causes cardiomyopathy or myocardial necrosis.

When isolated hearts are re-perfused with $Ca^{2+}$ containing medium after a short period of $Ca^{2+}$-free perfusion, contraction of myofibrils, loss of electrical activity, rupture of myocardial cells, flux of intracellular enzymes and the like are observed. This phenomenon was termed the "calcium paradox", and it has been suggested that the $Ca^{2+}$-overload played an important part in the occurrence of this phenomenon. Namely, it was proposed that the $Ca^{2+}$-overload causes cardiomyopathy at blood re-circulation after ischemia accompanied with ischemic heart diseases and heart operations. Finally the calcium paradox causes irreversible changes of myocardial cells. It was reported that this dysfunction resulting from the calcium paradox was reduced by drugs such as calcium antagonist.

The inventors have found that the aminoalkanesulfonic acid derivative of the present invention has an excellent protective effect against cardiomyopathy resulting from the $Ca^{2+}$-overload and improving effect on hypofunction of hearts in the low $Ca^{2+}$ concentration.

An object of the present invention is to provide a pharmacological composition for use in treating or preventing heart diseases, which comprises as an active ingredient an effective amount of at least one aminoalkanesulfonic acid derivative or pharmaceutically acceptable salt thereof. Another object of the invention is to provide the use of the aminoalkanesulfonic acid derivative and pharmaceutically acceptable salt thereof, for the manufacture of pharmaceutical composition for use in preventing or treating heart diseases in a mammal. Further object of the invention is to provide novel aminoalkanesulfonic acid derivatives or pharmaceutically acceptable salts thereof, which are useful as preventive medicine or remedy for various heart diseases.

DETAILED DESCRIPTION OF THE INVENTION

Figure 1:
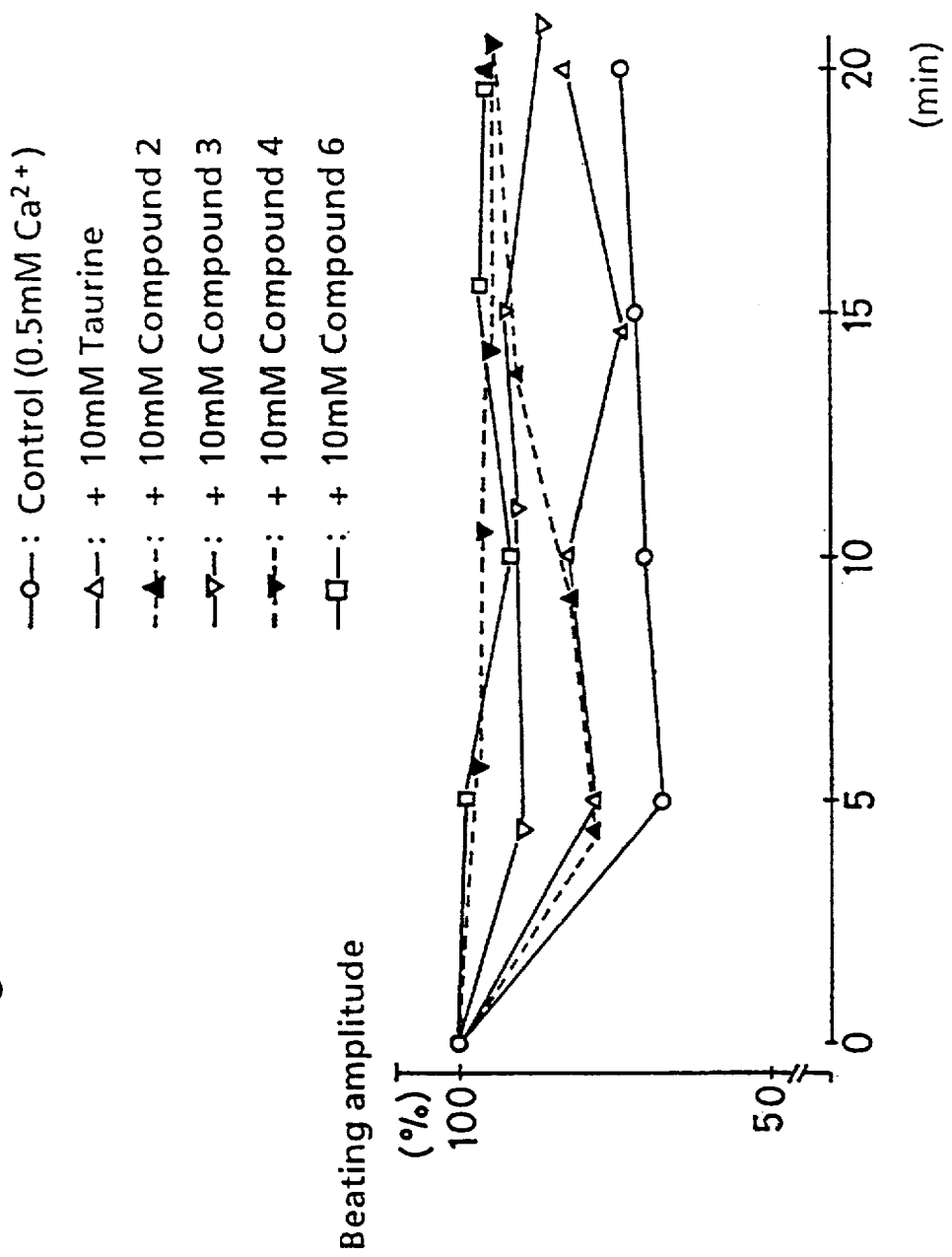
FIG. 1 illustrates the normalizing effects of the present invention against the lowering of pulse amplitude of myocardial cells in 0.5mM $Ca^{2+}$ medium.

The present invention mainly relates to a pharmaceutical composition for use in preventing or treating heart diseases in a mammal, which comprises at least one aminoalkanesulfonic acid derivative of the following formula (I) or pharmaceutically acceptable salt thereof.

$$\overset{X}{\underset{|}{HN}}-\overset{Y}{\underset{|}{CH}}-CH_2-SO_3H \quad (I)$$

In the formula (I), X is hydrogen or an amino acid residue, preferably glycine, alanine, valine, leucine, isoleucine, serine, threonine, methionine, proline, hydroxyproline, aspartic acid, β-aspartic acid, glutamic acid, γ-glutamic acid, phenylalanine, thyrosine and the like; Y is hydrogen, a phenyl group or an alkyl group, preferably a straight or branched alkyl group having 1 to 5 carbon atoms, such as methyl, ethyl, propyl, isopropyl, butyl, isobutyl, sec-butyl, t-butyl, pentyl, isopentyl, neo-pentyl or t-pentyl, which may have a hydroxy, amino, carboxy, phenyl or hydroxyphenyl group; or X and Y are joined to form a trimethylene or hydroxytrimethylene group; and at least one of X and Y is other than hydrogen.

Preferred compounds of the present invention are indicated as follows:

| No. | Name |
|---|---|
| 1 | Glycyltaurine |
| 2 | Alanyltaurine |
| 3 | Valyltaurine |
| 4 | Leucyltaurine |
| 5 | Isoleucyltaurine |
| 6 | Seryltaurine |
| 7 | Threonyltaurine |
| 8 | Methionyltaurine |
| 9 | Prolyltaurine |
| 10 | Hydroxyprolyltaurine |
| 11 | Aspartyltaurine |
| 12 | β-Aspartyltaurine |
| 13 | Glutamyltaurine |
| 14 | γ-Glutamyltaurine |
| 15 | Phenylalanyltaurine |
| 16 | Thyrosyltaurine |
| 17 | 2-Aminopropanesulfonic acid |
| 18 | 2-Amino-3-methylbutanesulfonic acid |
| 19 | 2-Amino-4-methylpentanesulfonic acid |
| 20 | 2-Amino-3-methylpentanesulfonic acid |
| 21 | 2-Amino-3-hydroxypropanesulfonic acid |
| 22 | 2-Amino-3-hydroxybutanesulfonic acid |
| 23 | 2-Pyrrolidinylmethanesulfonic acid |
| 24 | 2-(4-Hydroxypyrrolidinyl)methanesulfonic acid |
| 25 | 3-Amino-4-sulfobutyric acid |
| 26 | 4-Amino-5-sulfopentanoic acid |
| 27 | 2,6-Diaminohexanesulfonic acid |
| 28 | 2,5-Diaminopentanesulfonic acid |
| 29 | 2-Amino-3-phenylpropanesulfonic acid |
| 30 | 2-Amino-3-(4-hydroxypheny)propanesulfonic acid |
| 31 | 2-Amino-2-phenylethanesulfonic acid |

The aminoalkanesulfonic acid derivatives of the present invention include pharmaceutically acceptable salts of the compounds having formula (I) above, for example, salts as acid addition with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, glyconic acid, lactic acid, malonic acid, fumaric acid, anthranilic acid, benzoic acid, cinnamic acid, p-toluenesulfonic acid, naphthalenesulfonic acid or sulfanilic acid, salts with alkali metal such as sodium or potassium, salts with alkaline-earth metal such as calcium, magnesium or barium, or salts with other metals such as aluminum.

The aminoalkanesulfonic acid derivatives of this invention may also include their metal complexes, for example, complexes with zinc, nickel, cobalt, copper, iron etc.

These salts and metal complexes can be produced from free aminoalkanesulfonic acid derivatives in the usual way or can be interchanged with each other.

When optical isomers exist in the compounds of the invention, the present invention includes any types of isomers.

Several aminoalkanesulfonic acid derivatives of the present invention and a process for manufacturing them are disclosed in Chem. Pharm. Bull. 36(1), 70–77 (1988), Chem. Pharm. Bull. 36(8), 2796–2801 (1988), J. Chem. Soc. Perkin Trans. I, 1479–1481 (1989) and the like.

The aminoalkanesulfonic acid derivatives of the present invention include novel compounds represented by the following formula (I').

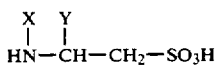

(I')

In the formula (I'), X is hydrogen or a methionyl group; Y is hydrogen, an isobutyl group, sec-butyl group, hydroxyethyl group, carboxyalkyl group such as carboxymethyl, carboxyethyl or carboxypropyl, aminoalkyl group such as aminomethyl, aminoethyl, aminopropyl or aminobutyl, or hydroxyphenylalkyl group such as hydroxyphenylmethyl or hydroxyphenylethyl; or X and Y are joined to form a trimethylene or hydroxytrimethylene group; and at least one of X and Y is other than hydrogen.

The said novel aminoalkanesulfonic acid derivatives may be produced according to the process disclosed in the above mentioned papers, and the physicochemical data of the embodiments of them are shown as follows. The specific rotation was measured using sodium lump ($\lambda = 5893$ Å).

EXAMPLES

Methionyltaurine (compound 8)

m.p.: 291°–293° C. (decomposition) $[\alpha]^{20}$: +34.3° (c=1.0, H$_2$O ) NMR(0.1NDCl, t-BuOD, $\delta$=1.23 ppm): $\delta$=2.10(3H,s), 2.09–2.24(2H,m), 2.60(1H,ddd,J=7 Hz, 7 Hz, 14 Hz), 2.63(1H,ddd,J=7 Hz, 7 Hz, 14 Hz), 3.11(2H,t,J=6.5 Hz), 3.62(1H,ddd,J=6.5 Hz, 6.5 Hz, 14 Hz), 3.66(1H,ddd,J=6.5 Hz, 6.5 Hz, 14 Hz), 4.10(1H,t,J=7 Hz) Elementary Analysis: C$_7$H$_{16}$N$_2$O$_4$S$_2$

|  | C % | H % | N % |
|---|---|---|---|
| Calculated | 32.80 | 6.29 | 10.93 |
| Found | 32.72 | 6.48 | 10.64 |

D-Methionyltaurine m.p.: 291°–293° C. (decomposition) $[\alpha]^{20}$: −34.2° (c=1.0, H$_2$O) Elementary Analysis: C$_7$H$_{16}$N$_2$O$_4$S$_2$

|  | C % | H % | N % |
|---|---|---|---|
| Calculated | 32.80 | 6.29 | 10.93 |
| Found | 32.94 | 6.43 | 11.03 |

2-Amino-4-methylpentanesulfonic acid (compound 19)
m.p.:>300° C. $[\alpha]^{20}$: +15.5° (c=1.0,H$_2$O) NMR(0.2 NNaOD, t-BuOD, $\delta$=1.23 ppm): $\delta$=0.89(3H,d,J=7 Hz), 0.90(3H,d,J=7 Hz), 1.30(2H,dd,J=7 Hz, 7 Hz), 1.67(1H,dqq,J=7 Hz, 7 Hz, 7 Hz), 2.78(1H,dd,J=9 Hz, 14 Hz), 3.01(1H,dd,J=3 Hz, 14 Hz), 3.29(1H,ddt,J=3 Hz, 9 Hz, 7 Hz)

Amino-3-methylpentanesulfonic acid (compound 20)
m.p.: 292°–293° C. $[\alpha]^{24}$: +24.8° (c=1.0, H$_2$O) Elementary Analysis: C$_6$H$_{15}$NO$_3$S

|  | C % | H % | N % |
|---|---|---|---|
| Calculated | 39.76 | 8.34 | 7.73 |
| Found | 39.81 | 8.52 | 7.62 |

NMR(0.2 NaOD, t-BuOD, $\delta$=1.23 ppm): $\delta$=0.86(3H,d,J=7.5 Hz), 0.89(3H,t,J=7.5 Hz), 1.12–1.24(1H,m), 1.31–1.42(1H,m), 1.46–1.57(1H,m), 2.75(1H,dd,J=10 Hz, 15 Hz), 3.03(1H,dd,J=2 Hz, 15 Hz), 3.15–3.20(1H,m)

2-Amino-3-hydroxybutanesulfonic acid (compound 22)
m.p.: 220°–222° C. $[\alpha]^{24}$: +15.5° (c=1.0, H$_2$O) Elementary Analysis: C$_4$H$_{11}$NO$_4$S

|  | C % | H % | N % |
|---|---|---|---|
| Calculated | 28.40 | 6.55 | 8.28 |
| Found | 28.10 | 6.35 | 7.95 |

NMR (0.2 NaOD, t-BuOD, $\delta$=1.23 ppm): $\delta$1.17(3H,d,J=6.5 Hz), 2.83(1H,dd,J=9 Hz, 14 Hz), 3.10(1H,dd,J=2.5 Hz, 14 Hz), 3.11–3.17(1H,m), 3.77–3.84(1 H,m) 2-Pyrrolidinylmethanesulfonic acid (compound 23) m.p.: 307°–308° C. (decomposition) $[\alpha]^{24}$: +33.4° (c=1.0, H$_2$O) Elementary Analysis: C$_5$H$_{11}$NO$_3$S

|  | C % | H % | N % |
|---|---|---|---|
| Calculated | 36.35 | 6.71 | 8.48 |
| Found | 36.43 | 6.94 | 8.37 |

NMR (0.2 NaOD, t-BuOD, $\delta$1.23 ppm): $\delta$=1.45(1H,ddd,J=8 Hz, 8 Hz, 9.5 Hz, 13 Hz), 1.67–1.83(2H,m), 2.20(1H,ddd,J=5 Hz, 7 Hz, 8 Hz, 13 Hz), 2.78(1H,ddd,J=7 Hz, 8 Hz, 10 Hz), 2.89(1H,ddd,J=6 Hz, 7 Hz, 10 Hz), 3.01(1H,dd,J=6.5 Hz, 14 Hz), 3.04(1H,dd,J=6.5 Hz, 14 Hz), 3.23–3.40(1H,m)

2-(4-Hydroxypyrrolidinyl)methanesulfonic acid (compound 24)
m.p.:>330° C. $[\alpha]^{20}$: +28.1° (c=1.0, H$_2$O) Elementary Analysis: C$_5$H$_{11}$NO$_4$S

|  | C % | H % | N % |
|---|---|---|---|
| Calculated | 33.14 | 6.12 | 7.73 |
| Found | 32.92 | 6.42 | 7.41 |

NMR (0.2 NaOD, t-BuOD, $\delta$=1.23 ppm): $\delta$=1.72(1H,ddd,J=6 Hz, 10 Hz, 14 Hz), 2.03(1H,ddt,J$_d$=6.5 Hz, 14 Hz,J$_t$=1.5 Hz), 2.75(1H,ddd,J=1 Hz, 3 Hz, 11.5 Hz), 3.01(1H,dd,J=7 Hz, 14 Hz), 3.08(1H,dd,J=6.5 Hz, 14 Hz), 3.15(1H,dd,J=5.5 Hz, 11.5 Hz), 3.60–3.68(1H,m), 4.40–4.45(1H,m)

3-Amino-4-sulfobutyric acid (compound 25)
m.p.: 266°–267° C. (decomposition) $[\alpha]^{23}$: −4.7° (c=1.0, H$_2$O) NMR (0.2 NaOD, t-BuOD, $\delta$=1.23 ppm): $\delta$=2.28(1H,dd,J=8.5 Hz, 15 Hz), 2.41(1H,dd,J=5.5 Hz, 15 Hz), 2.87(1H,dd,J=8.5 Hz, 14 Hz), 3.03(1H,dd,J=3 Hz, 14 Hz), 3.57(1H,dddd,J=3 Hz, 3.5 Hz, 5.5 Hz, 8.5 Hz)

4-Amino-5-sulfopentanoic acid (compound 26)

m.p.: 257°–258° C. (decomposition) $[\alpha]^{24}$: +16.9° (c=1.0, $H_2O$) Elementary Analysis: $C_5H_{11}NO_5S$

|  | C % | H % | N % |
|---|---|---|---|
| Calculated | 30.45 | 5.62 | 7.10 |
| Found | 30.30 | 5.89 | 6.95 |

NMR (0.2 NaOD, t-BuOD, $\delta$=1.23 ppm): $\delta$=1.97(2H,dt,$J_d$=7.5 Hz,$J_t$=7 Hz), 2.28–2.41(2H,m), 3.13(1H,dd,J=9.5 Hz, 15 Hz), 3.25(1H,dd,J=3 Hz, 15 Hz), 3.61–3.69(1H,m)

2,6-Diaminohexanesulfonic acid (compound 27)

m.p.: 192°–194° C. $[\alpha]^{23}$: +10.4° (c=1.0, $H_2O$) NMR (0.2 NaOD, t-BuOD, $\delta$=1.23 ppm): $\delta$=1.29–1.62(6H,m), 2.74–2.85(2H,m), 2.82(1H,dd,J=9 Hz, 14 Hz), 3.03(1H,dd,J=3 Hz, 14 Hz), 3.19–3.26(1H,m)

2,5-Diaminopentanesulfonic acid (compound 28)

m.p.: 277°–278° C. $[\alpha]^{24}$: +12.7° (c=1.0, $H_2O$) Elementary Analysis: $C_5H_{14}N_2O_3S \cdot HCl$

|  | C % | H % | N % |
|---|---|---|---|
| Calculated | 27.46 | 6.91 | 12.81 |
| Found | 27.49 | 6.97 | 12.86 |

NMR (0.2 NNaOD, t-BuOD, $\delta$=1.23 ppm): $\delta$=1.50(1H,dddd,J=6 Hz, 7 Hz, 9 Hz, 14 Hz), 1.61(1H,dddd,J=5 Hz, 6 Hz, 9 Hz, 14 Hz), 1.64–178(2H,m), 2.87(1H,dd,J=9 Hz, 14 Hz), 2.93(1H,ddd,J=7 Hz, 7 Hz, 13 Hz), 2.96 (1H,ddd,J=7 Hz, 7 Hz, 13 Hz), 3.04 (1H,dd,J=3.5 Hz, 14 Hz), 3.25 ( 1H,dddd,J=3.5 Hz, 5 Hz, 7 Hz, 9 Hz )

2-Amino-3- (4-hydroxypheny)propanesulfonic acid (compound 30)

m.p.:>330° C. $[\alpha]^{24}$: −4.7° (c=0.5, $H_2O$) Elementary Analysis: $C_9H_{13}NO_4S$

|  | C % | H % | N % |
|---|---|---|---|
| Calculated | 46.75 | 5.76 | 6.06 |
| Found | 46.68 | 5.86 | 6.16 |

NMR (0.2 NNaOD, t-BuOD, $\delta$=1.23 ppm): $\delta$=2.50(1H,dd,J=8 Hz, 14 Hz), 2.50(1 H,dd,J=8 Hz, 14 Hz), 2.69(1H,dd, 5.5 Hz, 14 Hz), 2.83(1H,dd, 9 Hz, 14 Hz), 3.06(1H,dd,J=3 Hz, 14 Hz), 3.38–3.45(1H,m), 5.56–661(2H,m), 6.99–7.03(2H,m)

The following examples, which are illustrative only and not intended to limit the scope of the invention, describe the preparation of the novel compounds of the present invention.

Example 1

7.48 g of t-butoxycarbonylmethionine and 5.91 g of N-hydroxy-5-norbornene-2,3-dicarboxyimide were dissolved in the mixture of 75 ml of tetrahydrofuran and 75 ml of dioxane. 6.81 g of dicyclohexylcarbodiimide was added thereto in an ice-cold water. The reaction mixture was stirred for 2 hours in an ice-cold water and 20 hours at room temperature. After the precipitated dicyclohexyl urea was filtered off, the solvent was evaporated under reduced pressure. The residue was dissolved in 75 ml dioxane. 50 ml of an aqueous solution of taurine sodium salt, which was prepared by 3.75 g of taurine and 2.52 g of sodium hydrogencarbonate, was added at room temperature and was stirred for 20 hours. After the insoluble material was filtered off, the solvent was evaporated under reduced pressure. The residue was dissolved in 100 ml of water, and washed with ethyl acetate. The aqueous layer was passed through cation-exchange resins to desalt and remove the protecting group. The eluent was evaporated under the reduced pressure, and the residue was treated with 4N hydrogen chloride/dioxane. After evaporation of the solvent, the precipitated white crystals were obtained by filtration with ethanol, and recrystallized with the mixture of water and ethanol to give 5.34 g of methionyltaurine (compound 8)

In the same manner, D-methionyltaurine was obtained.

Example 2.

(1) Under argon atmosphere, 11.8 g of N-benzyloxycarbonyl-L-prolinol and 13.9 g of triphenylphosphine were dissolved in 150 ml of tetrahydrofuran. In an ice-cold water, 8.4 ml of diethyl azodicarbonate, and then 3.8 ml of thioacetic acid were added. After stirring for 2 hours in an ice-cold water and for 20 hours at room temperature, the solvent was evaporated under reduced pressure. The residue was purified with silica gel column chromatography to give 11.96 g of 2-(1-benzyloxycarbonylpyrrolidinyl)methyl ethanethioate as an oily substance.

(2) A performic acid solution was prepared by stirring 24 ml of 30% aqueous solution of hydrogen peroxide and 240 ml of 98% formic acid for one hour at room temperature. This solution was cooled, and then a formic acid solution of the said 2-(1-benzyloxycarbonylpyrrolidinyl)methyl ethanethioate was added dropwise during 30 minutes. After stirring for 2 hours in an ice-cold water and for 20 hours at room temperature, 5 g of 10% Pd/C was added to decompose excess peroxide. Further Pd/C was added, and the solution was stirred for 10 hours under hydrogen atmosphere. After the catalyst was filtered off, the solvent was evaporated under reduced pressure to give 5.78 g of 2-Pyrrolidinylmethanesulfonic acid (compound 23) as white crystals.

In the same manner, the compounds 19, 20, 22, 24, 25, 26, 27, 28 and 30 were obtained.

The following descriptions serve to illustrative pharmacological studies of the compounds of the present invention.

(1) The heart was removed from 14- to 16-day-old mouse fetus (ICR strain) and was cut in small pieces. The medium containing 0.06% trypsin and 0.01% collagenase was added, and incubated for 10 minutes at 37° C. to disperse the cells. Eagle's minimum essential medium (Eagle MEM) supplemented with 10% fetal bovine serum was added and the cells were collected by centrifugation and dispersed again in a culture medium. Since the attachment time of myocardial cells is different from that of fibroblast-like cells, the dispersed cell solution was incubated for one hour at 37° C. under a water-saturated atmosphere of 5% $CO_2$ in the air and the fibroblast-like cells were removed. The obtained myocardial cells were pre-incubated at a concentration of from $2 \times 10^5$ to $4 \times 10^5$ cells per one milliliter and then used in the $Ca^{2+}$ paradox test.

After the culture medium was removed, one milliliter of EGTA medium ($Ca^{2+}$-free) containing a test compound was added and incubated for 10 minutes at 20° C. -22° C. Then the cells were washed with $Ca^{2+}$-free medium containing the test compound and no EGTA, then the medium was rapidly replaced by 1 mM $Ca^{2+}$ medium, and morphological changes such as blebs, balloon formation etc. of the cells were observed one minute after.

The results are shown in Table 1 and Table 2.

TABLE 1

| Test compound | The percentage of cells showing morphological changes (%) |
|---|---|
| control | 47.4 ± 3.5 |
| compound 1 (10 mM) | 33.2 ± 0.8 |
| compound 2 (10 mM) | 40.5 ± 5.3 |
| compound 3 (10 mM) | 37.4 ± 0.7 |
| compound 4 (10 mM) | 40.3 ± 1.9 |
| compound 5 (10 mM) | 40.7 ± 2.8 |
| compound 6 (10 mM) | 43.4 ± 2.3 |
| compound 8 (10 mM) | 27.9 ± 2.7 |
| compound 9 (10 mM) | 35.6 ± 4.2 |
| compound 10 (10 mM) | 28.2 ± 2.7 |
| compound 11 (10 mM) | 40.3 ± 4.9 |
| compound 12 (10 mM) | 38.2 ± 3.0 |
| compound 13 (10 mM) | 32.6 ± 3.0 |
| compound 14 (10 mM) | 36.7 ± 1.7 |
| compound 15 (10 mM) | 34.3 ± 4.2 |

TABLE 2

| Test compound | The percentage of cells showing morphological changes (%) |
|---|---|
| control | 51.4 ± 2.4 |
| compound 17 (10 mM) | 34.0 ± 2.0 |
| compound 18 (10 mM) | 42.8 ± 4.2 |
| compound 19 (10 mM) | 41.4 ± 4.2 |
| compound 20 (10 mM) | 36.2 ± 4.2 |
| compound 21 (10 mM) | 36.6 ± 2.4 |
| compound 22 (10 mM) | 40.2 ± 2.6 |
| compound 23 (10 mM) | 28.5 ± 1.5 |
| compound 24 (10 mM) | 38.8 ± 2.8 |
| compound 25 (10 mM) | 32.8 ± 3.8 |
| compound 26 (10 mM) | 33.6 ± 2.5 |
| compound 28 (10 mM) | 33.7 ± 1.5 |
| compound 29 (10 mM) | 40.9 ± 2.5 |
| compound 30 (10 mM) | 46.3 ± 3.5 |
| compound 31 (10 mM) | 42.5 ± 2.9 |

(2) The pulse amplitude of myocardial cells was lowered by replacing the culture medium with low $Ca^{2+}$ medium. The test compound was added to the low $Ca^{2+}$ medium (0.5 mM $Ca^{2+}$) and its effect on the lowered pulse amplitude of myocardial cells was studied. An example of the results is shown in FIG. 1.

As clearly shown by the results in Table 1 and Table 2, the aminoalkanesulfonic acid derivatives of the present invention have excellent protective effects on myocardial cells against morphological changes caused by the $Ca^{2+}$ paradox. And the results in FIG. 1 show that the compounds of this invention significantly reduced the lowering of pulse amplitude of myocardial cells induced in the low $Ca^{2+}$ culture medium.

Thus the compounds of the present invention have protective effect against myocardial disorders caused by $Ca^{2+}$-overload and the like, and also normalizing effect on myocardial cells, i.e. reduce the lowering of pulse amplitude of myocardial cells. Therefore, the aminoalkanesulfonic acid derivatives are useful as preventive medicine or remedy for various heart diseases, for example, ischemic heart disease such as myocardial infarction, myocardial disorders under ischemic state during the heart operation, heart failure, angina pectoris and the like.

What is claimed is:

1. An aminoalkanesulfonic acid derivative of the formula:

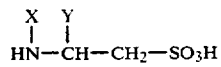

wherein (1) when X is hydrogen, Y is an isobutyl, sec-butyl, hydroxyethyl, aminopropyl, aminobutyl or hydroxyphenylalkyl group; (2) when X is a methionyl group, Y is hydrogen, an isobutyl, sec-butyl, hydroxyethyl, carboxyalkyl, aminoalkyl or hydroxyphenylalkyl group; or (3) X and Y are joined to form a hydroxytrimethylene group;

or a pharmaceutically acceptable salt thereof.

2. An aminoalkanesulfonic acid compound according to claim 1, wherein X is hydrogen.

3. An aminoalkanesulfonic acid compound according to claim 1, wherein X is a methionyl group.

4. An aminoalkanesulfonic acid compound according to claim 1, wherein X and Y are joined to form a hydroxytrimethylene group.

5. A method for preventing or treating heart diseases in a mammal, which comprises administering to the mammal an effective amount of at least one aminoalkanesulfonic acid compound of the formula:

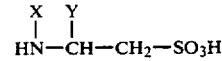

wherein X is hydrogen, a glycyl, alanyl, valyl, leucyl, isoleucyl, seryl, threonyl, methionyl, prolyl, hydroxyprolyl, aspartyl, β-aspartyl, glutamyl, γ-glutamyl, phenylalanyl or thyrosyl group; Y is hydrogen, a phenyl group or an alkyl group, which may be substituted by a hydroxy, amino, phenyl or hydroxyphenyl group; or X and Y are joined to form a trimethylene or hydroxytrimethylene group; and at least one of X and Y is other than hydrogen, or a pharmaceutically acceptable salt thereof.

* * * * *